United States Patent
Ebina

(10) Patent No.: US 10,850,132 B2
(45) Date of Patent: Dec. 1, 2020

(54) PARTICLE THERAPY SYSTEM

(71) Applicant: Hitachi, Ltd., Tokyo (JP)

(72) Inventor: Futaro Ebina, Tokyo (JP)

(73) Assignee: HITACHI, LTD., Tokyo (JP)

( * ) Notice: Subject to any disclaimer, the term of this patent is extended or adjusted under 35 U.S.C. 154(b) by 36 days.

(21) Appl. No.: 16/158,342

(22) Filed: Oct. 12, 2018

(65) Prior Publication Data
US 2019/0126074 A1    May 2, 2019

(30) Foreign Application Priority Data

Oct. 30, 2017    (JP) .................................. 2017-209642

(51) Int. Cl.
| | | |
|---|---|---|
| *A61N 5/10* | (2006.01) | |
| *H05H 13/04* | (2006.01) | |
| *H05H 7/04* | (2006.01) | |
| *H05H 7/10* | (2006.01) | |

(52) U.S. Cl.
CPC .......... *A61N 5/1081* (2013.01); *A61N 5/1077* (2013.01); *H05H 7/04* (2013.01); *H05H 7/10* (2013.01); *H05H 13/04* (2013.01); *A61N 2005/1087* (2013.01); *H05H 2007/045* (2013.01); *H05H 2277/10* (2013.01)

(58) Field of Classification Search
CPC ................ A61N 5/1081; A61N 5/1077; A61N 2005/1087; H05H 7/10; H05H 7/04; H05H 13/04; H05H 2277/10; H05H 2007/045

See application file for complete search history.

(56) References Cited

U.S. PATENT DOCUMENTS

| | | | | |
|---|---|---|---|---|
| 5,001,438 A | * | 3/1991 | Miyata | H05H 7/18 313/11 |
| 5,363,008 A | * | 11/1994 | Hiramoto | H05H 7/10 313/62 |
| 5,436,537 A | * | 7/1995 | Hiramoto | H05H 7/08 315/507 |
| 5,483,129 A | * | 1/1996 | Yamamoto | H05H 7/04 250/396 R |
| 6,008,499 A | * | 12/1999 | Hiramoto | H05H 13/04 250/492.3 |
| 6,087,670 A | * | 7/2000 | Hiramoto | H05H 13/04 250/396 ML |
| 9,155,186 B2 | * | 10/2015 | Zwart | H05H 7/04 |

(Continued)

FOREIGN PATENT DOCUMENTS

JP    10-162999 A    6/1998

*Primary Examiner* — Brooke Purinton
(74) *Attorney, Agent, or Firm* — Mattingly & Malur, PC

(57) ABSTRACT

A particle therapy system in which the efficiency of extracting a beam from a synchrotron can be improved and time required for therapy can be shortened is provided. The synchrotron 10 of the particle therapy system 100 extracts a charged particle beam, which circulates in the synchrotron 10, out of the synchrotron 10 by means of a slow extraction method using the resonance of a betatron oscillation, and magnetic poles 73 included in a bending magnet 12 of the synchrotron 10 have a SIM structure that generates a magnetic field distribution that makes the horizontal tune of the charged particle more closely approach a resonant line used in the slow extraction method as the amplitude of the horizontal betatron oscillation of a charged particle included in the charged particle beam becomes larger.

6 Claims, 12 Drawing Sheets

(56) References Cited

U.S. PATENT DOCUMENTS

| | | | | |
|---|---|---|---|---|
| 9,185,789 B2* | 11/2015 | Zwart | .................... | H05H 13/02 |
| 10,086,214 B2* | 10/2018 | Balakin | ................ | A61N 5/1039 |
| 2007/0170994 A1* | 7/2007 | Peggs | .................... | H05H 13/04 |
| | | | | 331/34 |
| 2012/0013274 A1* | 1/2012 | Bertozzi | ................ | H05H 13/08 |
| | | | | 315/504 |
| 2015/0231411 A1* | 8/2015 | O'Neal, III | .......... | A61N 5/1043 |
| | | | | 600/1 |
| 2015/0343238 A1* | 12/2015 | Balakin | ................ | A61N 5/1082 |
| | | | | 600/1 |
| 2016/0213950 A1* | 7/2016 | Ebina | .................... | A61N 5/1048 |
| 2016/0330827 A1* | 11/2016 | Sugahara | ................ | H05H 7/04 |

* cited by examiner

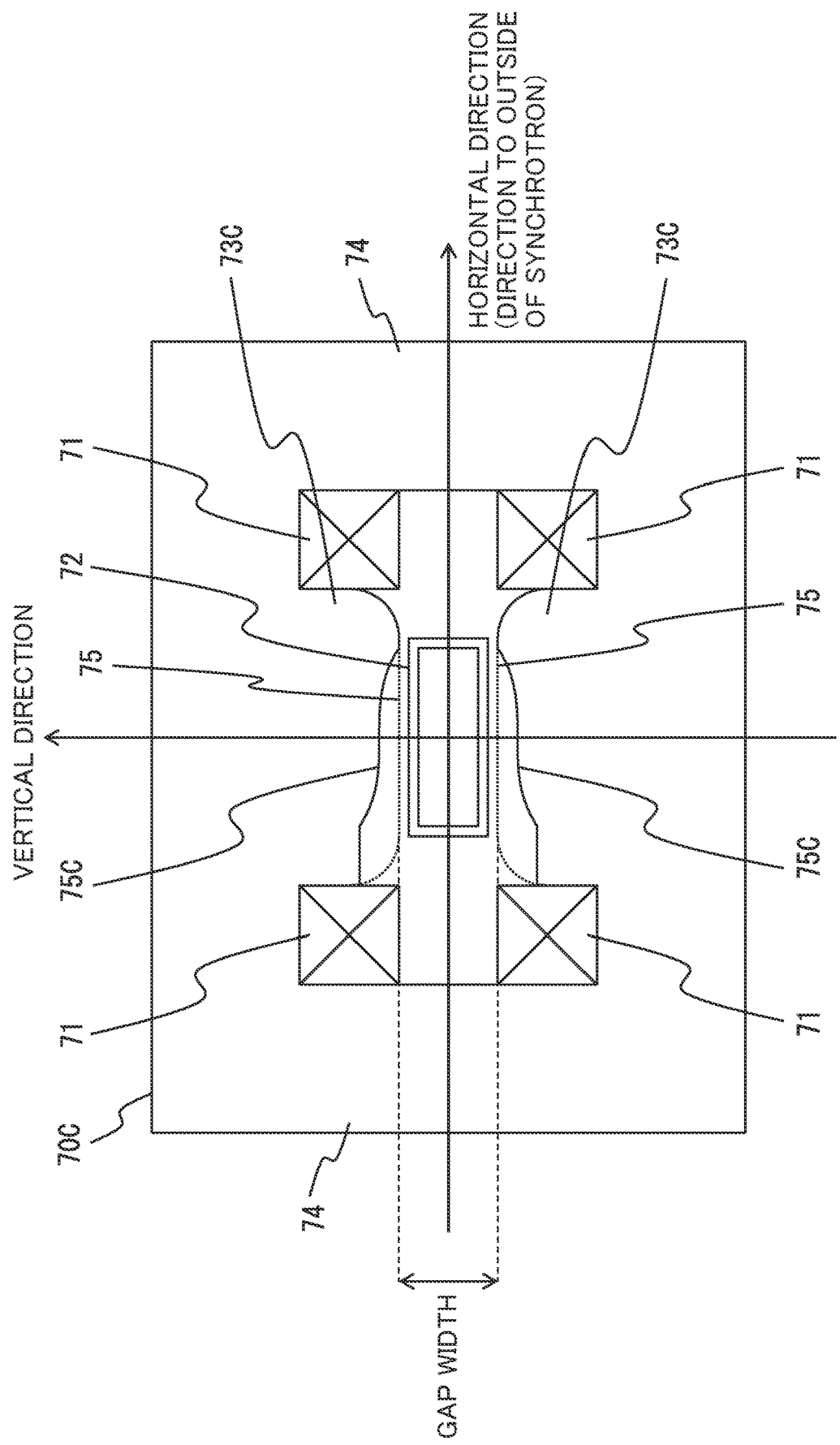

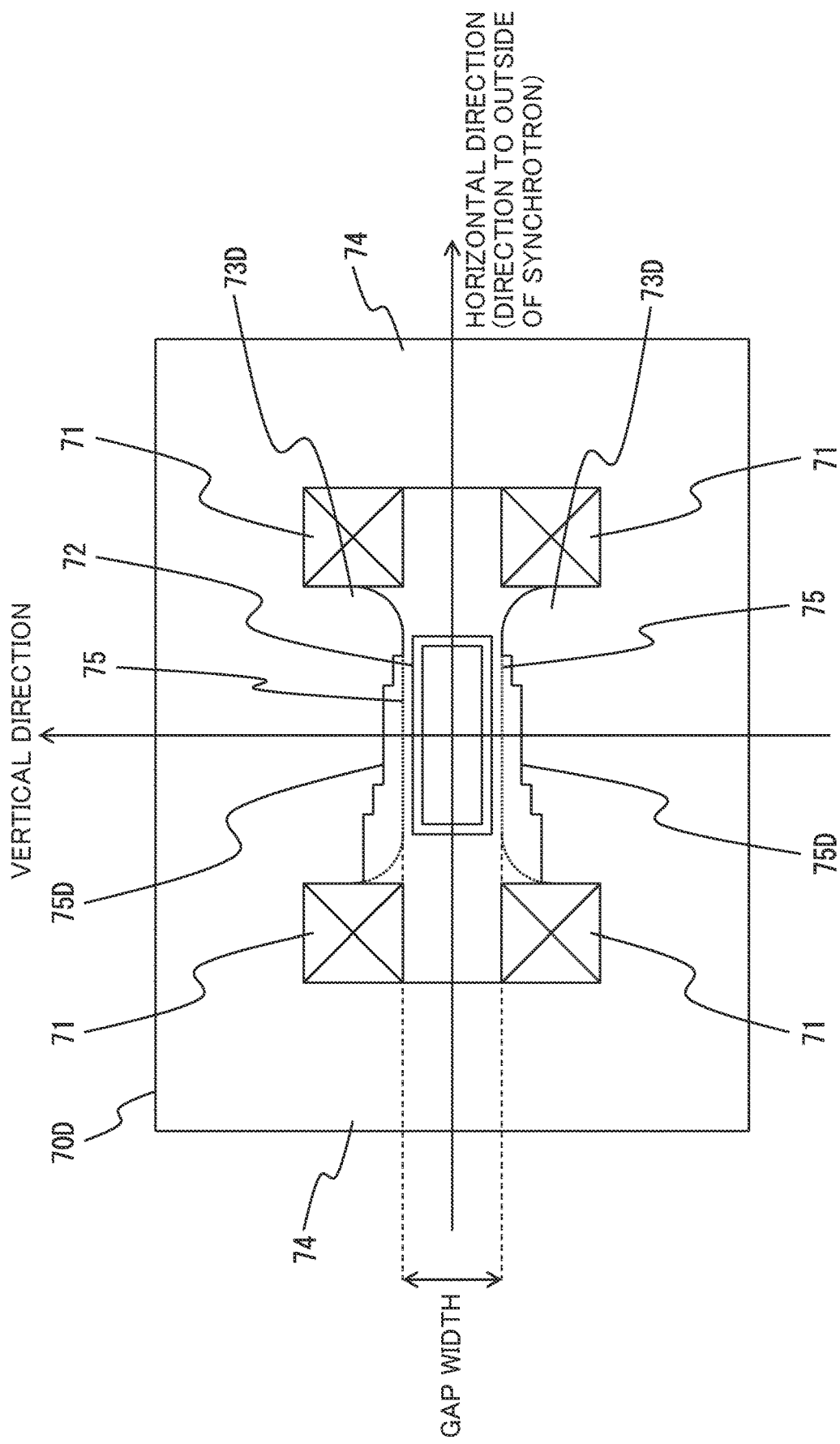

PARTICLE THERAPY SYSTEM

TECHNICAL FIELD

The present invention relates to particle therapy systems.

BACKGROUND ART

One of background arts in this technological field is a technology disclosed in Patent Literature 1.

Patent Literature 1 discloses a technology in which, in order to provide a synchrotron type accelerator having high charged particle beam extraction efficiency and a medical device using the same by decreasing the beam loss of the charged particle beam, an accelerator includes: a quadruple convergence magnet that decides the stability limit of resonance; quadruple divergence magnets; a resonance excitation multipole magnet; a radiofrequency acceleration system for beam extraction for making the stability limit transcended by increasing a betatron oscillation; a beam extraction electrostatic bending device; and a beam extraction bending magnet, and two quadruple divergence magnets and a bending magnet are installed between the electrostatic bending device and the beam extraction bending magnet, and the bending magnet is installed between the two quadruple divergence magnets.

CITATION LIST

Patent Literature

Patent Literature 1: Japanese Unexamined Patent Application Publication Hei 10-162999

SUMMARY OF INVENTION

Technical Problem

The abovementioned Patent Literature 1 discloses a particle therapy system in which a stability limit (a separatrix) for the resonance of a betatron oscillation is formed in a phase space in the horizontal direction of a synchrotron, and a horizontal radiofrequency voltage is fed to a beam that circulates in the synchrotron (a circulating beam) to enlarge the betatron oscillation amplitude of a circulating particle, with the result that the circulating beam particle that transcends the separatrix is bent by an electrostatic deflector and a septum magnet and extracted.

In the particle therapy system disclosed in the abovementioned Patent Literature 1, the area of the separatrix for extraction is kept constant during the beam extraction period, therefore it becomes possible to keep the orbit and the current value of the beam extracted from the synchrotron stable.

On the other hand, in the particle therapy system disclosed in the abovementioned Patent Literature 1, since circulating beam particles having the large amplitudes of horizontal betatron oscillations are lost when the separatrix for extraction is formed, there is room to improve the efficiency of extracting beams from the synchrotron.

This problem that the efficiency of extracting beams is lowered due to a beam loss during the separatrix being formed appears conspicuously especially in the case where the beams are extracted in a low energy state (for example, 70 MeV in the case of photon therapy) where the horizontal emittance of the circulating beam is not sufficiently attenuated.

As for this problem, to enlarge the area of the separatrix for extraction is useful for lowering the beam loss when the separatrix is formed.

In this case, however, because the horizontal distance (a turn separation) between a circulating beam particle and an extracted beam particle is decreased, and the ratio of beam particles that are lost due to the collision of the beam particles with the electrodes of the electrostatic deflector increases, there is also room to improve the efficiency of extracting beams.

Therefore, an object of the present invention is to provide a particle therapy system in which the efficiency of extracting a beam from a synchrotron can be improved and time required for therapy can be shortened.

Solution to Problem

The present invention includes plural means for solving the abovementioned problem, and one example of the plural means is a particle therapy system to be hereinafter described. The particle therapy system is a system in which an irradiation target is irradiated with a charged particle beam after the charged particle beam is accelerated by a synchrotron, the synchrotron extracts the charged particle beam, which circulates in the synchrotron, out of the synchrotron by means of a slow extraction method using the resonance of a betatron oscillation, the synchrotron includes at least one bending magnet that bends the charged particle beam, and magnetic poles included in the bending magnet have a shim structure that generates a magnetic field distribution that makes the horizontal tune of the charged particle more closely approach a resonant line used in the slow extraction method as the amplitude of the horizontal betatron oscillation of a charged particle included in the charged particle beam becomes larger.

Advantageous Effects of Invention

According to the present invention, it becomes possible to provide a particle therapy system in which the efficiency of extracting a beam from a synchrotron can be improved and time required for therapy can be shortened.

Problems, configurations, and advantageous effects other than those described above will be explicitly shown by explanations about the following embodiments.

BRIEF DESCRIPTION OF DRAWINGS

FIG. 11 is a schematic diagram showing the cross-sectional view of a bending magnet which is included in the synchrotron of the particle therapy system according to the second embodiment and that is viewed from the vertical positive direction.

FIG. 12 is a schematic diagram showing the cross-sectional view of a bending magnet which is included in the synchrotron of the particle therapy system according to the second embodiment and that is viewed from the vertical positive direction.

DESCRIPTION OF EMBODIMENTS

Hereinafter, the embodiments of a particle therapy system according to the present invention will be explained with reference to the accompanying drawings.

First Embodiment

A first embodiment of the particle therapy system of the present invention will be explained with reference to FIG. 1 to FIG. 9.

Figure 1:
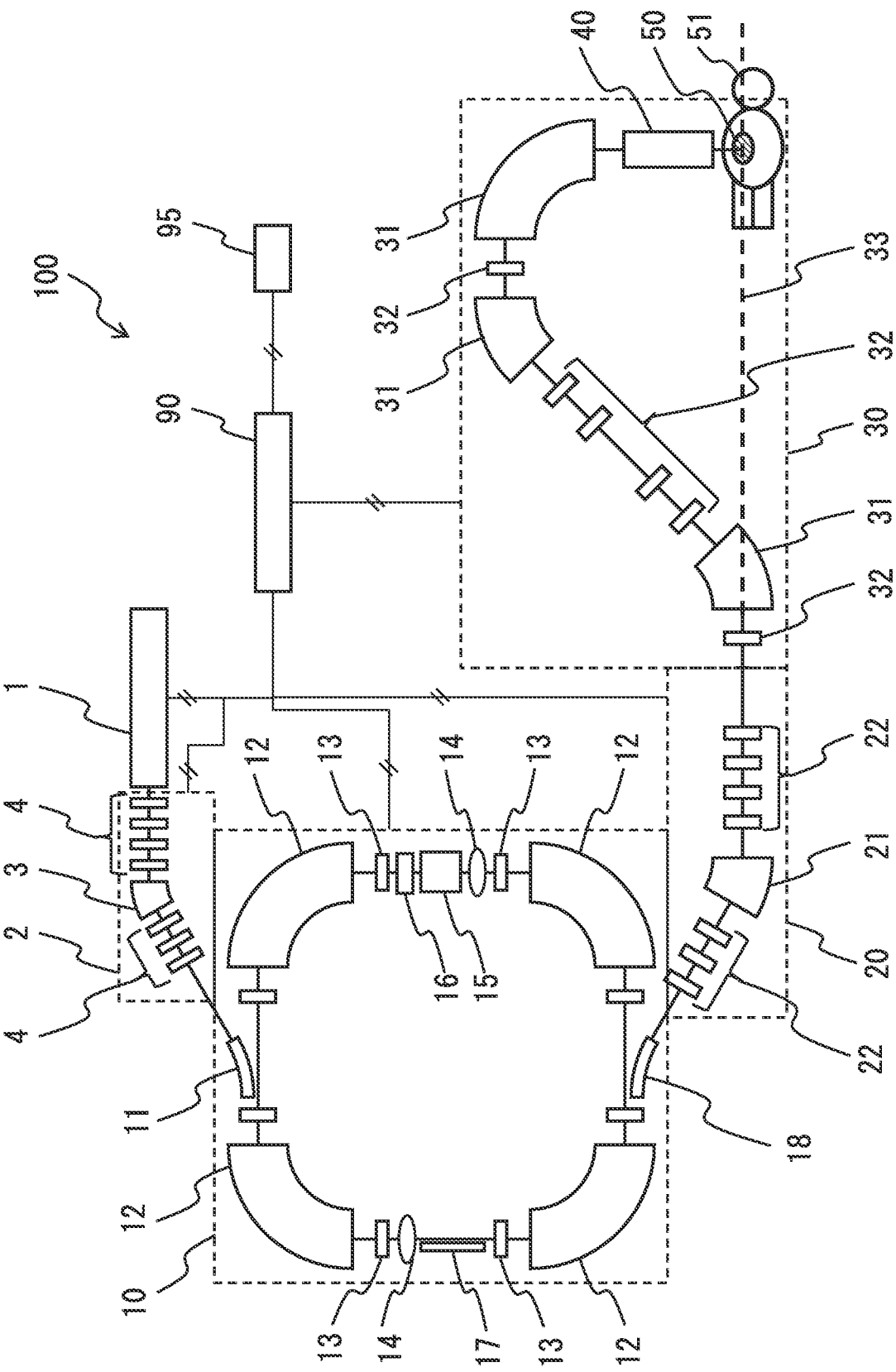
FIG. 1 is a diagram showing an example of the configuration of a particle therapy system according to a first embodiment of the present invention.

First, the overall configuration of the particle therapy system will be explained with reference to FIG. 1. FIG. 1 is a diagram showing an example of the configuration of the particle therapy system according to this embodiment.

In FIG. 1, a particle therapy system 100 according to this embodiment is a system in which a charged particle beam (referred to as a beam hereinafter) that is injected from an injector 1 is accelerated by a synchrotron 10 so that the beam builds up its energy into predefined kinetic energy (kinetic energy will be referred to as energy for short hereinafter), the beam is extracted to a high energy beam transport 20, and the target volume 51 of a patient 50 is irradiated with the beam after the beam passed through a rotating gantry 30 and a beam delivery system/nozzle/irradiation nozzle 40 mounted on the rotating gantry 30.

The behaviors of respective mechanisms in the particle therapy system 100 are controlled by a control apparatus 90. Especially, it should be noted that the control of the extraction of the beam from the synchrotron 10 is also performed by this control apparatus 90, which will be described later.

A linear accelerator (LINAC) that accelerates a beam generated at an ion source (not shown) so that the beam builds up its energy into energy suitable for the beam to be injected into the synchrotron 10 (referred to as incident energy hereinafter) is used as the injector 1, for example. It will be assumed that the beam includes a proton, or a heavy particle ion such as a helium ion or a carbon ion that is heavier than a proton.

The charged particle beam extracted from the injector 1 is injected into the synchrotron 10 via a low energy beam transport 2 and an inflector 11 for injection. The low energy beam transport 2 includes a bending magnet 3 that bends the beam toward the synchrotron 10, quadrupole magnets 4 that adjust the shape of the beam so that the shape of the beam becomes suitable for being injected into the synchrotron 10, and the like.

The synchrotron 10 is composed of the inflector 11 for injection, plural bending magnets 12, plural quadrupole magnets 13, plural sextupole magnets 14, a radiofrequency acceleration cavity 15, a radiofrequency voltage feeding device 16 for extraction, an electrostatic deflector 17 for extraction, a septum magnet 18 for extraction, and the like.

The bending magnets 12 bend a beam that circulates in the synchrotron 10 (the beam that circulates in the synchrotron is referred to as a circulating beam and) in such a way that the beam forms a predefined circulating orbit (this predefined circulating orbit is referred to as a circulating beam orbit hereinafter).

Figure 4:
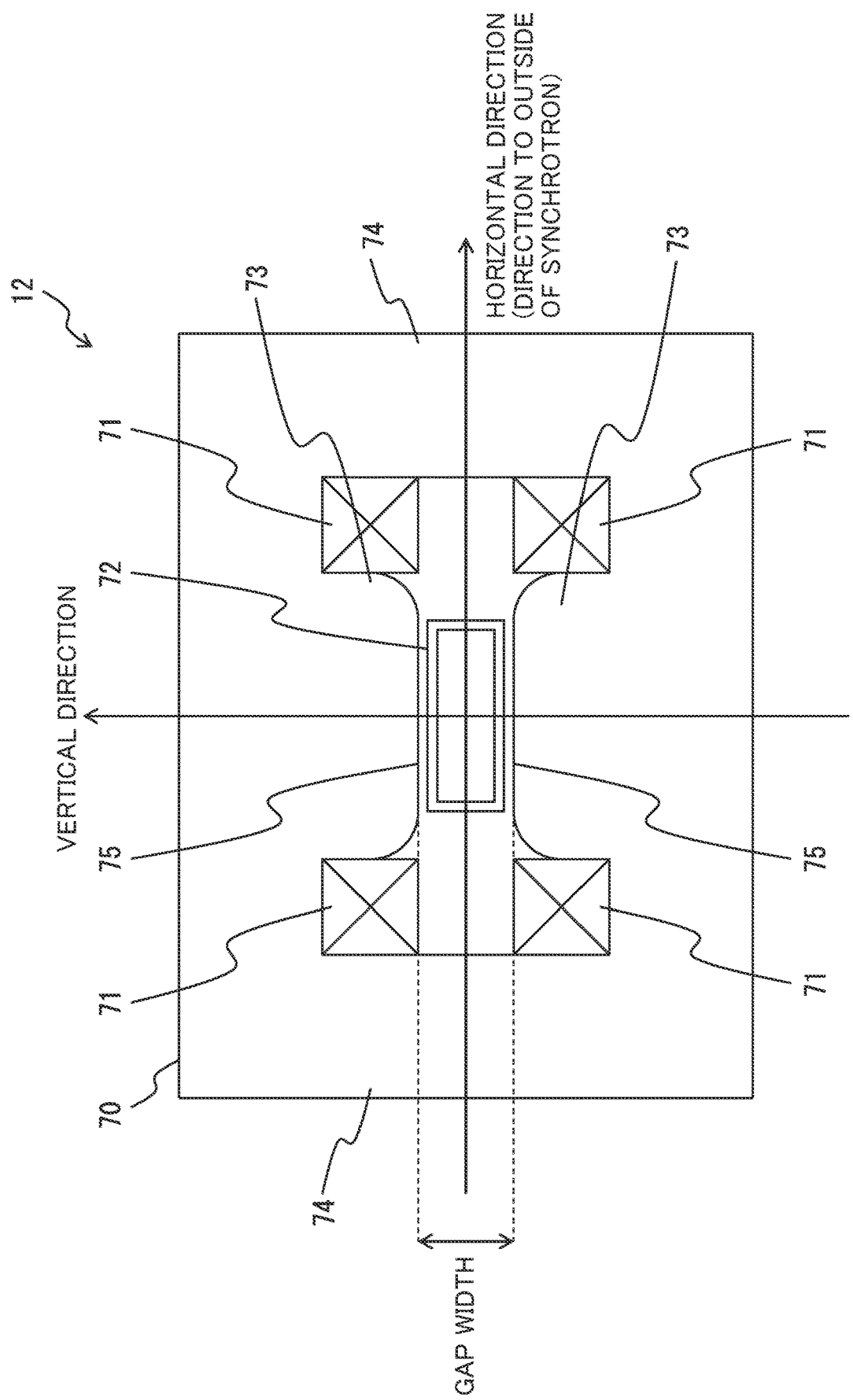
FIG. 4 is a cross-sectional schematic view taken along the line A-A in FIG. 3.

In the present invention, a direction taken along the traveling direction of the circulating beam will be referred to as a traveling direction (a direction in which the beam travels is the positive direction of the traveling direction), a direction that is perpendicular to the traveling direction and that is taken along the radial direction of a bending magnet 12 will be referred to as a horizontal direction (a direction to the outside of the synchrotron is the positive direction), and a direction perpendicular to both traveling direction and horizontal direction will be referred to as a vertical direction (a direction to the top of FIG. 4 is the positive direction).

In addition, in the synchrotron, the circulating beam orbit defined in design is referred to as a central orbit. A circulating beam particle vibrates in the horizontal direction or in the vertical direction around the central orbit, and this vibration is called a betatron oscillation. Furthermore, the vibration number of the betatron oscillation per lap of the synchrotron is referred to as a tune.

The quadrupole magnets 13 keep the tune of a circulating beam a constant value that makes the circulating beam stable by applying force to the circulating beam so that the circulating beam converges or diverges.

The radiofrequency acceleration cavity 15 captures the circulating beam in a predefined phase in the traveling direction of the circulating beam by feeding a radiofrequency voltage in the traveling direction (the fed radiofrequency voltage will be referred to as an acceleration voltage, and capturing the circulating beam in the predefined phase will be referred to as a radiofrequency capturing hereinafter), and accelerates the circulating beam to the extent that the circulating beam has predefined energy.

The momentum of the circulating beam particle, which is captured in the radiofrequency capturing, vibrates with a momentum calculated in design as a center (the momentum calculated in design will be referred to as a central momentum hereinafter), and this vibration is called the synchrotron oscillation of the circulating beam particle. During a period while the circulating beam is being accelerated, the excitation amounts of the bending magnets 12 and the excitation amounts of the quadrupole magnets 13 are increased in proportion to the momentum of the circulating beam, and at the same time, the frequency of the acceleration voltage (referred to as an acceleration frequency hereinafter) is controlled so that the frequency has a suitable value for keeping the circulating beam orbit and the tune of the circulating beam constant respectively.

After the acceleration of the circulating beam is finished, the synchrotron 10 changes the excitation amounts of the quadrupole magnets 13 so that the horizontal tune of the circulating beam approaches a value that makes the circulating beam unstable (the value will be referred to as a resonant line for extraction hereinafter).

Figure 2:
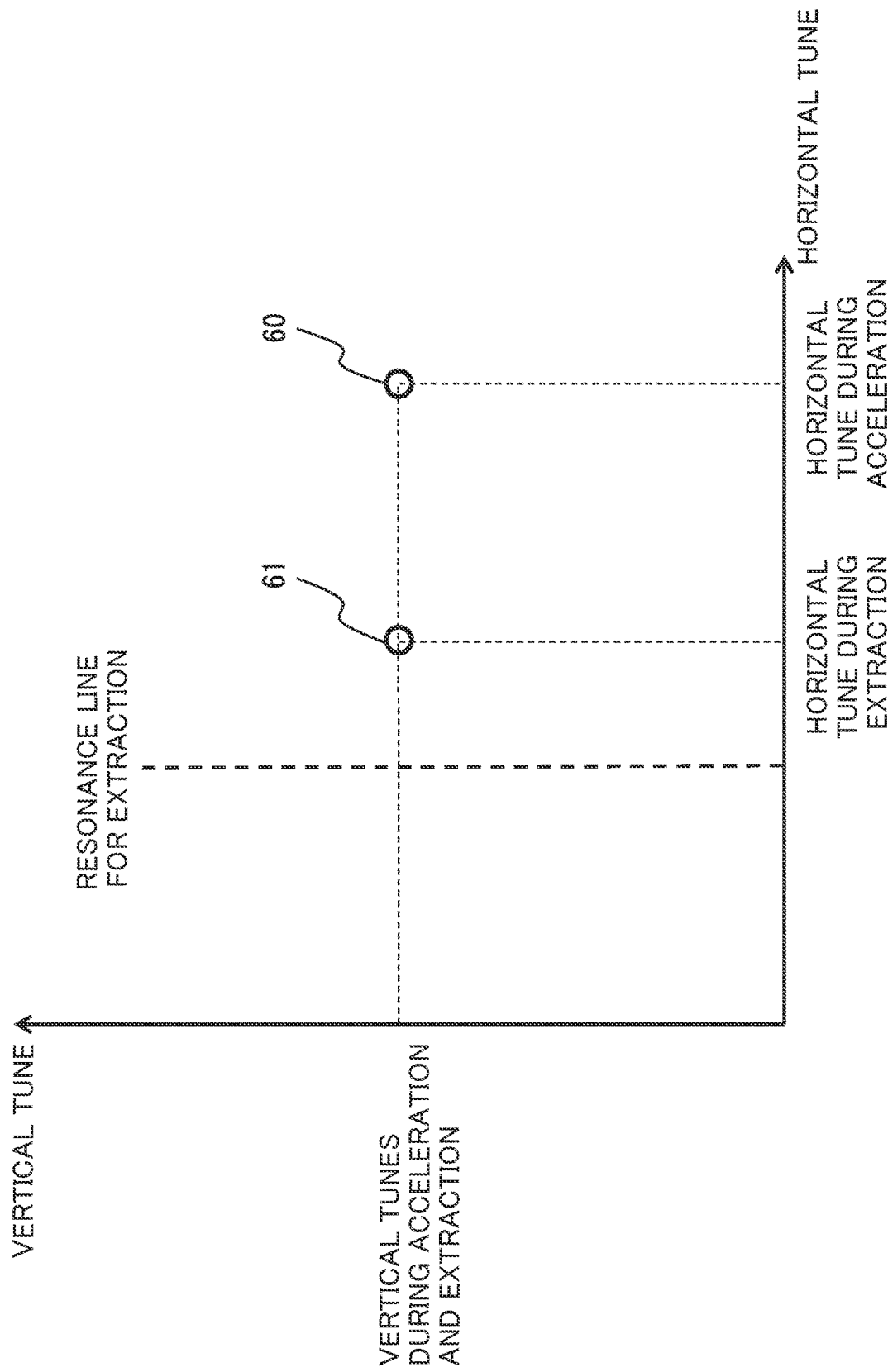
FIG. 2 is a schematic diagram showing the relationship between a resonant line for extraction and the horizontal tune of a synchrotron in the particle therapy system according to the first embodiment.

The relationship between the horizontal tune and the vertical tune of the synchrotron 10 and the resonant line for extraction is shown in FIG. 2. The horizontal axis in FIG. 2 represents the horizontal tune of the synchrotron 10, the vertical axis represents the vertical tune of the synchrotron 10, a white circle 60 represents a combination of the horizontal tune and the vertical tune when a circulating beam is accelerated (an operating point), and a white circle 61 represents a combination of the horizontal tune and the vertical tune when a circulating beam is extracted.

In this embodiment, the horizontal tunes when a circulating beam is accelerated have values higher than the resonant line for extraction. In addition, the horizontal tunes when the circulating beam is extracted are controlled by the quadrupole magnets 13 so that the horizontal tunes become higher than the resonant line for extraction, and they become lower than the horizontal tunes when the circulating beam is accelerated (that is to say, they become nearer to the resonant line for extraction). The synchrotron 10 excites the sextupole magnets 14 to feed the magnetic field the intensity of which is proportional to the square of the distance from the central orbit to a circulating beam (this magnetic field will be referred to as a sextupole magnetic field hereinafter), and forms the stability limit of the betatron oscillation (referred to as a separatrix hereinafter) of a circulating beam particle in a phase space defined by the horizontal direction position and gradient of the circulating beam particle.

The radiofrequency voltage feeding device 16 feeds a horizontal direction radiofrequency voltage the frequency of which is synchronized with the horizontal tunes of the circulating beam particles to the circulating beam, and amplifies the amplitudes of the horizontal betatron oscillations of the circulating beam particles. Circulating beam particles, the amplitudes of the horizontal betatron oscillations of which were increased to transcend the separatrix, abruptly increase the amplitudes of their betatron oscillations and enter the electrostatic deflector 17.

The electrostatic deflector 17 deflects the incoming circulating beam particles to the horizontal direction, and makes the incoming circulating beam particles enter the septum magnet 18.

The septum magnet 18 further deflects the beam particles that have already deflected by the electrostatic deflector 17 to the horizontal direction, and extracts the beam particles out of the synchrotron 10. Here, it is also possible to use a Lambertson magnet that deflects the beam to the vertical direction instead of the septum magnet 18. Furthermore, the septum magnet 18 can be composed of plural magnets.

The beam extracted from the synchrotron 10 (referred to as an extracted beam hereinafter) is irradiated to the target volume 51 of a patient after the beam passes through the high energy beam transport 20, the rotating gantry 30, and the beam delivery system/nozzle/irradiation nozzle 40 mounted on the rotating gantry 30.

The high energy beam transport 20 includes a bending magnet 21, quadrupole magnets 22, and the like, and transports the extracted beam from the synchrotron 10 to the inlet of the rotating gantry 30.

The rotating gantry 30 includes bending magnets 31, quadrupole magnets 32, and the like, and the beam delivery system/nozzle/irradiation nozzle 40 is mounted on the terminal end of the rotating gantry 30. The rotating gantry 30 is set rotatable with a rotating axis 33 as its rotation axis, and beams incoming from the high energy beam transport 20 can be irradiated to the target volume 51 from plural different directions.

The beam delivery system/nozzle/irradiation nozzle 40 reshapes the beam transported through the high energy beam transport 20 and the rotating gantry 30, and forms an irradiation dose distribution (referred to as a radiation field hereinafter) that is fitted into the shape of the target volume 51 of a patient. In the particle therapy system according to this embodiment, a scanning irradiation method in which a beam is scanned so as to fit the shape of the target volume 51 is adopted to form the radiation field.

In the scanning irradiation method, through changing the energy of a beam irradiated to the patient 50, the depth of the body of a patient 50 which the beam reaches is controlled. In this embodiment, in order to change the energy of a beam irradiated to the patient 50, the energy of the beam when the beam is extracted from the synchrotron 10 is changed.

Nevertheless, the irradiation method used in the beam delivery system/nozzle/irradiation nozzle 40 is not limited to the scanning irradiation method, and various heretofore known irradiation methods and configurations can be used for the beam delivery system/nozzle/irradiation nozzle 40. In addition, the beam delivery system/nozzle/irradiation nozzle 40 can be configured to be used not only in the state of being rotated but also in the state of being fixed. Furthermore, the high energy beam transport 20 is not indispensable for the particle therapy system according to this embodiment, and a beam can be extracted directly from the synchrotron 10 to the beam delivery system/nozzle/irradiation nozzle 40.

After the extraction of a circulating beam is finished, the synchrotron 10 changes the excitation amounts of the bending magnets 12, the excitation amounts of the quadrupole magnets 13, and the setting value of the acceleration frequency into their respective values at the time when the circulating beam enters the synchrotron 10 in order to prepare for the incoming of the next beam. A period between the time when a beam enters the synchrotron 10 and the time when the next beam enters the synchrotron 10 will be referred to as a cycle of the synchrotron 10.

The particle therapy system 100 according to this embodiment repeats the acceleration, extraction, and irradiation of beams until the radiations of beams are performed the number of times predefined by a treatment planning system 95.

The configuration and control for improving the efficiency of extracting beams from the synchrotron 10 in the particle therapy system 100 according to this embodiment will be explained hereinafter.

Figure 3:
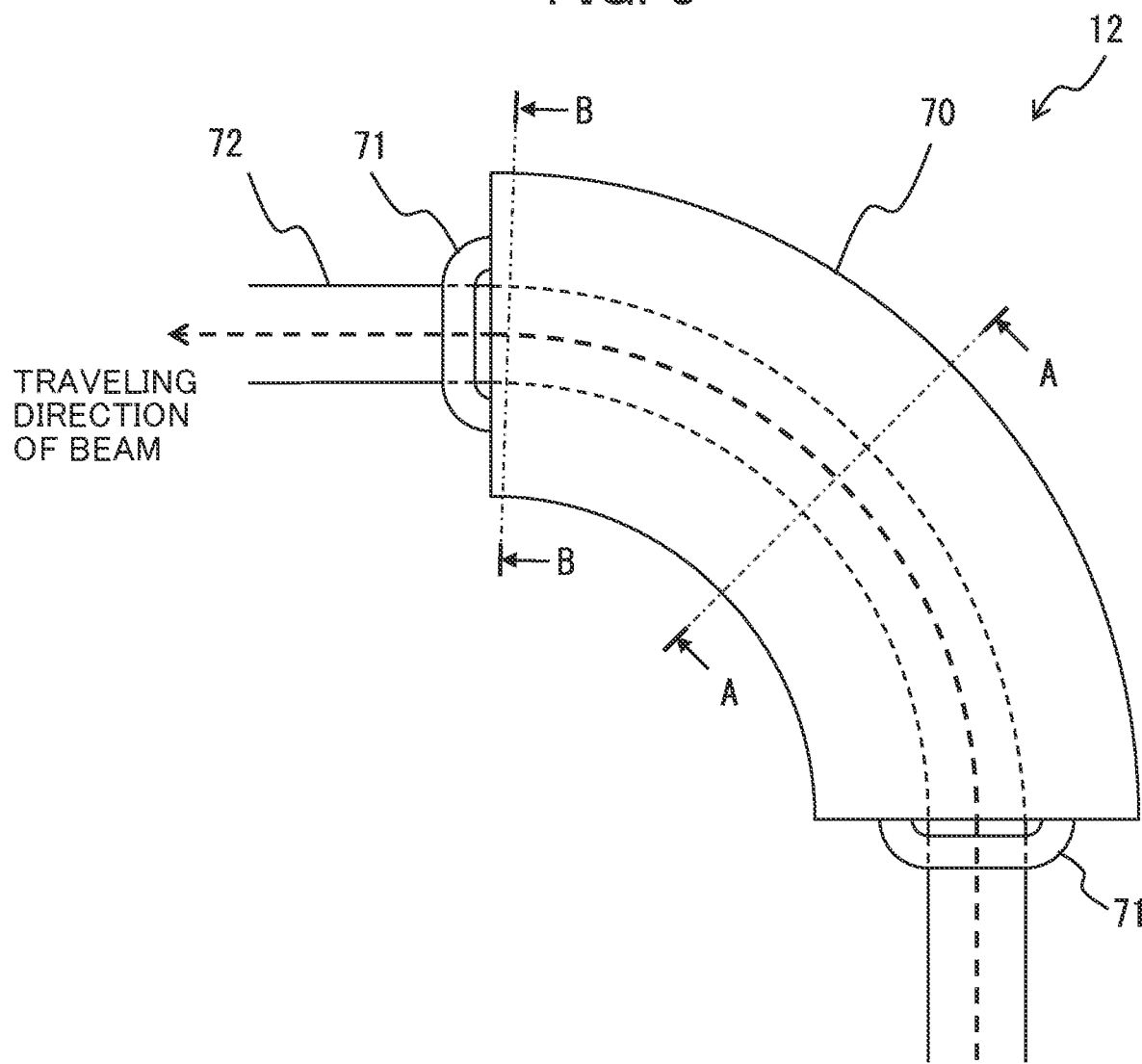
FIG. 3 is a schematic diagram showing a bending magnet which is included in the synchrotron of the particle therapy system according to the first embodiment and that is viewed from the vertical positive direction.

FIG. 3 is a schematic diagram showing a bending magnet 12 which is included in the synchrotron 10 and that is viewed from the vertical positive direction (from vertically above).

As shown in FIG. 3, the bending magnet 12 includes a magnetic body 70 and a coil 71, and a vacuum duct 72, through which a circulating beam passes, runs completely through the magnet body 70.

The schematic diagram of a cross-sectional view of the bending magnet 12 obtained by cutting the central part of the bending magnet 12 in the traveling direction using a plane perpendicular to the traveling direction of the circulating beam (taken along the line A-A) is shown in FIG. 4.

As shown in FIG. 4, the magnetic body 70 includes magnetic poles 73 and return yokes 74, and a gap, through which the vacuum duct 72 passes, is formed between the magnetic poles 73. The magnetic poles 73 are symmetrical to each other about a horizontal plane (a plane on which the central orbit of the synchrotron 10 is located).

Planes facing the horizontal planes of the magnetic poles 73 are referred to as magnetic pole surfaces 75, and a distance between intersection points of a line parallel to the vertical direction and the magnetic pole surfaces 75, that is to say, a distance between two magnetic surfaces 75 at each horizontal direction position is referred to as a gap width.

At the central part of the bending magnet 12 in the traveling direction, the gap width of the bending magnet 12 in the range where the vacuum duct 72 is inserted, that is to say, in the range where the beam passes is approximately constant regardless of the horizontal direction position of the gap.

Since the intensity of the magnetic field generated by the bending magnet 12 is inversely proportional to the gap width, the bending magnet 12 generates approximately constant bending magnetic field at the central part of the bending magnet 12 in the traveling direction regardless of the horizontal direction position of the gap.

Figure 5:
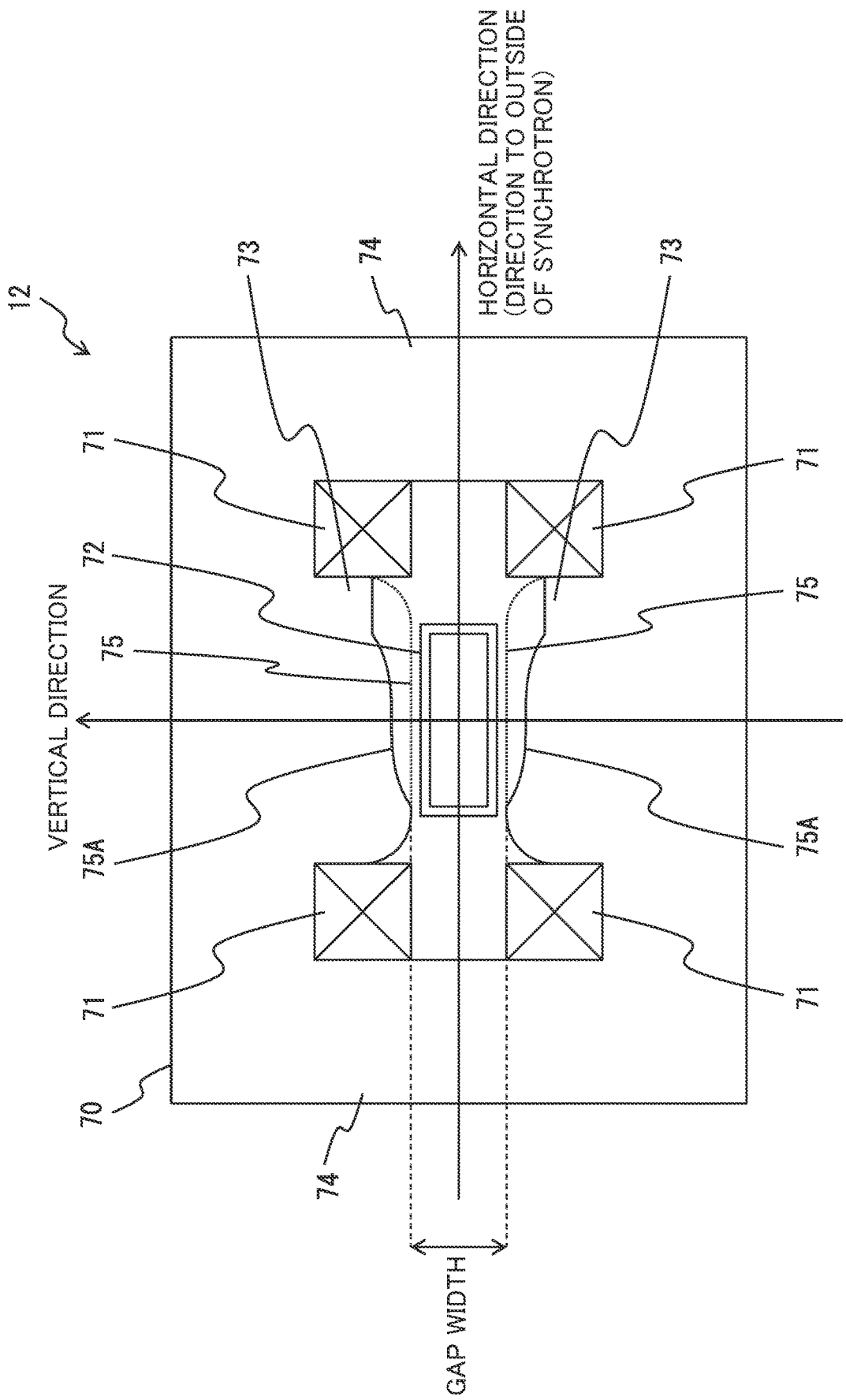
FIG. 5 is a cross-sectional schematic view taken along the line B-B in FIG. 3.

The schematic diagram of a cross-sectional view of the bending magnet 12 obtained by cutting the traveling direction end of the bending magnet 12 (the outlet side of the circulating beam) using a plane perpendicular to the traveling direction of the circulating beam (taken along the line B-B) is shown in FIG. 5. The shapes of the magnetic poles 73 (the vertical direction position of the magnetic pole surfaces 75) at the central part of the bending magnet 12 (the cross-sectional part taken along the line A-A) are shown in FIG. 5 for the purpose of reference.

As shown in FIG. 5, although the structures of the magnetic body 70 at the ends of a bending magnet 12 are similar to the structure of the magnetic body 70 at the central part of the bending magnet 12 in the traveling direction, the gap width varies depending on the horizontal direction position of the gap at the ends of the bending magnet 12.

To put it concretely, at the end of the bending magnet 12, a gap width that is a distance between magnetic pole surfaces 75A of the magnetic poles 73 in a region at the horizontal direction positive side of the central orbit (outside in the radial direction) is wider than a gap width on the central orbit, and a gap width that is a distance between magnetic pole surfaces 75A of the magnetic poles 73 in a region at the horizontal direction negative side of the central orbit (inside in the radial direction) is narrower than the gap width on the central orbit.

Such a shim structure is formed in such a way that the abovementioned gap widths do not become smaller than the gap width at the central part of the bending magnet 12 in the traveling direction (in the vicinity of the cross-section taken the line A-A in FIG. 3). As described above, in this embodiment, the size of the vacuum duct 72 in the vertical direction is prevented from becoming smaller due to the above shim structure, which makes it easy to control the circulating beam, and at the same time, makes it easy to form the vacuum duct 72.

Figure 6:
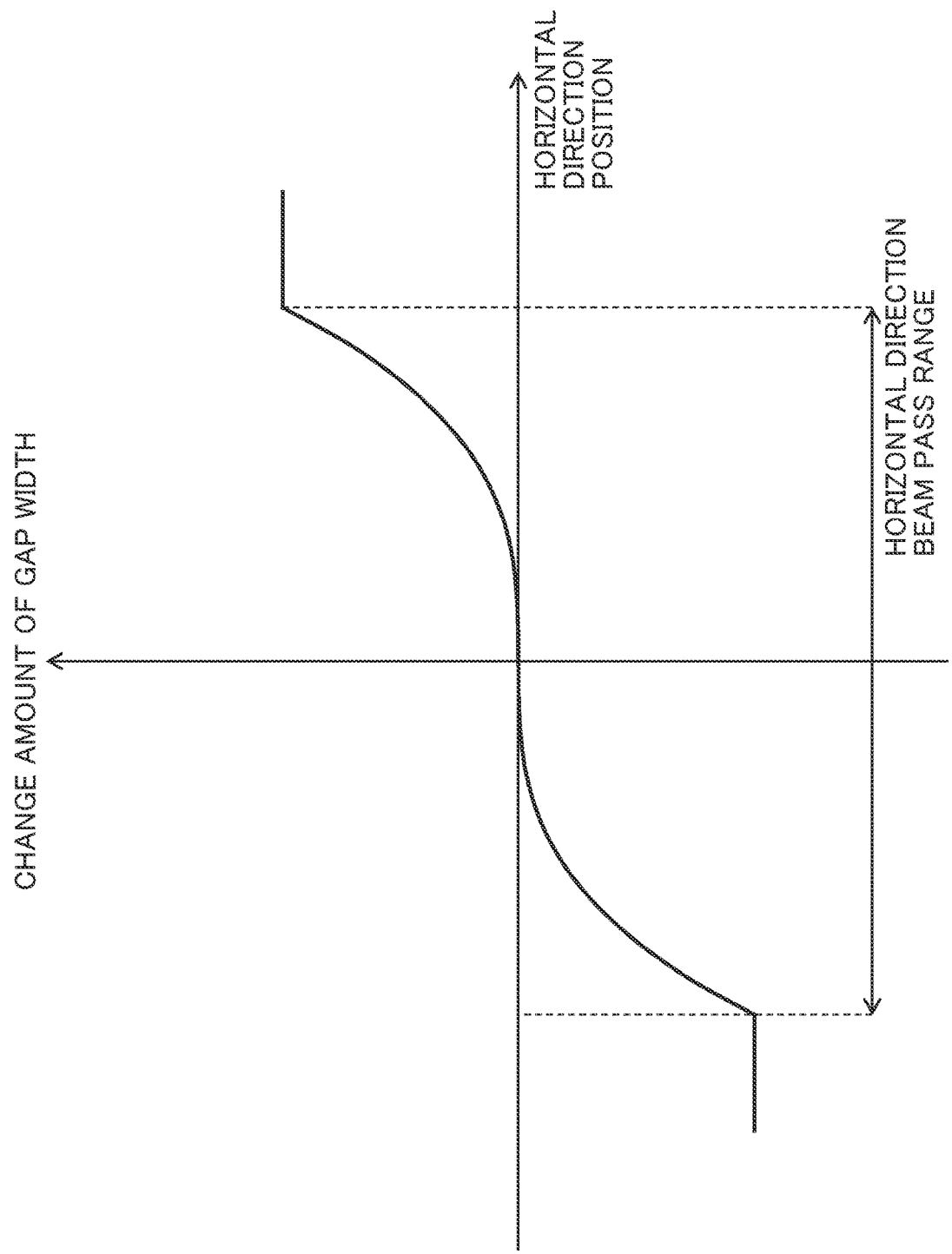
FIG. 6 is a diagram showing the relationship between the horizontal direction position and the change amount of the gap width of a gap at the traveling direction end of the bending magnet of the particle therapy system according to the first embodiment.

FIG. 6 shows a diagram showing the relationship between the horizontal direction position of a gap and the change amount of the gap width of the gap at the traveling direction end of the bending magnet 12.

As shown in FIG. 6, the change amount of the gap width in the range through which the beam passes has a cubic function shape, and the change amount of the gap width is proportional to the cube of the horizontal direction distance from the central orbit. Since the intensity of the magnetic field generated by a bending magnet 12 is inversely proportional to the gap width, a magnetic field the intensity of which is proportional to the cube of the horizontal direction distance from the central orbit, that is to say, a so-called octupole magnetic field is generated in addition to the primary bending magnetic field at the end of the bending magnet 12.

The structure of magnetic poles 73 that has the change of a gap width depending on the horizontal position at the end of the bending magnet 12 at the outlet side of the circulating beam and superimposes a multipole magnetic field on a bending magnetic field as mentioned above is referred to as a shim structure of the bending magnet 12.

As for the direction of the octupole magnetic field generated by the shim structure, a beam is deflected to the positive horizontal direction (the direction makes the bending magnetic field weakened) in the region of the positive horizontal direction viewed from the central orbit, and the beam is deflected to the negative horizontal direction (the direction makes the bending magnetic field strengthened) in the region of the negative horizontal direction viewed from the central orbit. Therefore, the octupole magnet field that makes a circulating beam diverge in the horizontal direction is generated by the shim structure of the bending magnet 12.

A divergent force a circulating beam particle receives from the octupole magnetic field generated by such a shim structure is approximately proportional to the square of the amplitude of the horizontal betatron oscillation of the circulating beam particle.

When a horizontal direction divergent force is applied to a circulating beam particle, the horizontal tune of the circulating beam particle is decreased proportionally to the divergent force. Therefore, in the synchrotron 10 according to this embodiment, the larger the amplitude of the horizontal betatron oscillation of a circulating beam particle is, the more drastically the horizontal tune of the circulating beam particle is decreased due to the octupole magnetic field generated by the shim structure of the bending magnet 12.

As described above, in the synchrotron 10 according to this embodiment, since the value of the horizontal tune of a circulating beam particle when the beam is extracted is higher than the value of the resonant line for extraction, the shim structure of the bending magnet 12 generates a magnetic field distribution that makes the horizontal tune of a circulating beam particle more closely approach the resonant line for extraction as the amplitude of the horizontal betatron oscillation of the circulating beam particle becomes larger.

Such a shim structure as shown in FIG. 5 is also formed at the end of the inlet side of the bending magnet 12 for the circulating beam. Because two shim structures are formed at both inlet side and outlet side of the circulating beam, the change amount of a gap width can be set smaller in comparison with the case where one shim structure is formed at either of the two sides, therefore it becomes possible to suppress necessity to change the vertical direction width of the vacuum duct 72 depending on the traveling direction of the circulating beam by forming the shim structures in the abovementioned way. In addition, it is easier to form the shim structures in this way than in the case where a shim structure is formed uniformly along the traveling direction of the circulating beam as described latter, with the result that the shim structures can be formed more accurately in the former case than in the latter case.

Nevertheless, although it is desirable that shim structures of the bending magnet 12 should be formed both at the inlet side and at the outlet side of a circulating beam, it is also conceivable that a shim structure is formed at either of the two sides. In this case, it is desirable that the change amount of a gap width in the radial direction should be double the change amount of a gap width in the case of shim structures being formed both at the inlet side and at the outlet side.

Considering the case of two shim structures being formed both at the inlet side and at the outlet side of the circulating beam of the bending magnet 12 and the case of one shim structure being formed at either of the two sides, it is desirable that a region in which a shim structure is formed should be a region to which a process for uniformizing a magnetic field, a so-called Rogowski cut, is applied. Here, the Rogowski cut can have a curved shape or a step-like shape, and the shape of the Rogowski cut is not limited to a special one.

Furthermore, a shim structure is formed not only at the inlet side or at the outlet side, but also it is formed uniformly along the traveling direction of a circulating beam. In this case, it is desirable that the change amount of the gap width of the shim structure in the radial direction should be uniform regardless of the traveling direction of the circulating beam.

In addition, it will be assumed that shim structures having the same structures are formed at the inlet sides and at the outlet sides of all bending magnets 12 in the synchrotron 10 according to this embodiment. Since all the bending magnets 12 installed in the synchrotron 10 have the shim structures having the same structures, particularly it becomes unnecessary to respectively change the control parameters of the plural quadrupole magnets 13 and the plural sextupole magnets 14 that are installed other than the bending magnets 12, therefore an advantageous effect that the control of the circulating beam becomes easier can be achieved.

Nevertheless, it is not necessarily indispensable that the positions and shapes of the shim structures formed in all the bending magnets 12 are the same in the traveling direction of the circulating beam, and the respective positions and shapes can be modified accordingly.

An advantageous effect that is brought about by the fact that the horizontal tune of a circulating beam particle more closely approaches the resonant line for extraction as the amplitude of the horizontal betatron oscillation of the circulating beam particle becomes larger will be explained hereinafter with reference to FIG. 7 and FIG. 8.

Figure 7:
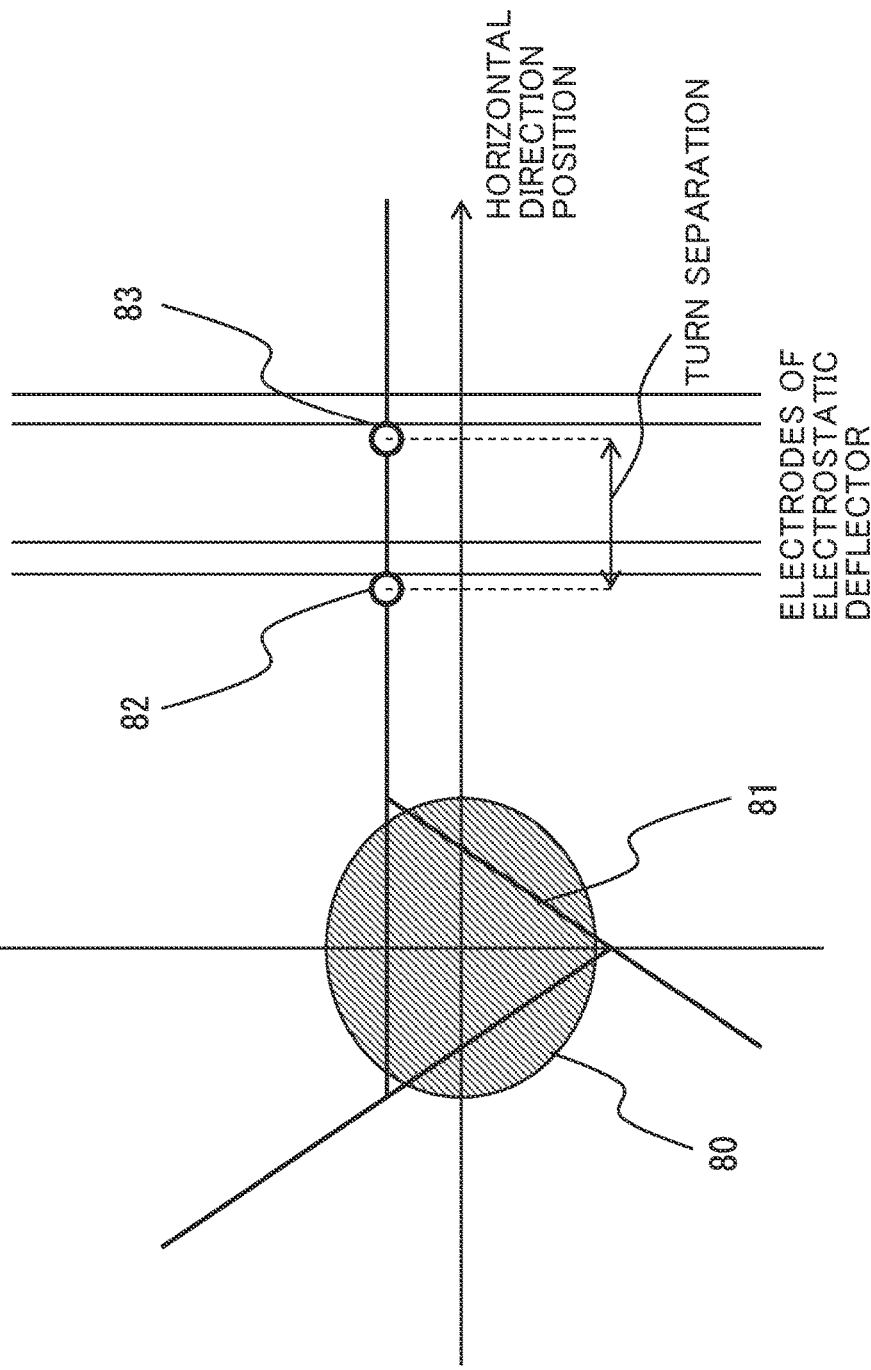
FIG. 7 is a schematic diagram of the horizontal direction phase space distribution of circulating beam particles at the inlet position of an electrostatic deflector of a related particle therapy system.

FIG. 7 is a schematic diagram showing the horizontal direction phase space distribution of circulating beam particles at the inlet side of an electrostatic deflector in the case where the influence brought about by the shim structures of the bending magnets 12 is not taken into consideration, that is to say, at the inlet side of a related electrostatic deflector for comparison. The horizontal axis of FIG. 7 represents the horizontal direction position of a circulating beam particle and the vertical axis represents the change rate of the horizontal direction position along the traveling direction of a beam (referred to as the horizontal direction gradient hereinafter).

An ellipse 80 in FIG. 7 shows the existence range of circulating beam particles at the time when the acceleration of the circulating beam particles is finished. A triangle 81 shows a border between the stable region of a betatron oscillation generated by the sextupole magnets and the unstable region (a separatrix).

As for circulating beam particles that move outside the separatrix during an extraction period, the amplitudes of the horizontal betatron oscillations of the circulating beams abruptly increase and the circulating beams enter the electrostatic deflector, with the result that the circulating beams are extracted from the synchrotron. Lines extending from the separatrix (the branches of the separatrix) represents the sets of points in a phase space through which circulating beam particles pass during a period from the time when the circulating beam particles transcend the separatrix and to the time when the circulating beam particles enter the electrostatic deflector.

A white circle 82 represents a position of a certain circulating beam particle in the phase space, in which the certain circulating beam particle has transcended the separatrix and is about to start running three laps of the synchrotron before entering the electrostatic deflector, and a white circle 83 represents a position in the phase space which a certain circulating beam particle located at the white circle 82 will reach after running three laps of the synchrotron. The maximum value of horizontal direction distances between the white circle 82 and the white circle 83 will be referred to as a turn separation.

Since the orbits of beam particles extracted from the synchrotron are continuously distributed on the branches of the separatrix, some of the beam particles collide with the electrodes of the electrostatic deflector and they are lost in the process of the extraction of beam particles. In order to improve the efficiency of the extraction of beam particles from the synchrotron, it is necessary to set the value of the turn separation almost equal to the value of the distance between the electrodes of the electrostatic deflector.

The amplitudes of the horizontal betatron oscillations of circulating beam particles that are located outside of the separatrix at the time when the acceleration is finished abruptly increase during the formation of the separatrix and the circulating beam particles are lost.

Furthermore, strictly speaking, since the separatrix for extraction has not yet been formed at the time when the acceleration is finished, it cannot be judged weather or not a circulating beam particle at the time when the acceleration is finished is located outside of the separatrix. In this case, if the amplitude of the horizontal betatron oscillation of a circulating beam particle at the time when the acceleration is finished is larger than the amplitude of the horizontal betatron oscillation of a circulating beam particle located inside of the separatrix for extraction, the former circulating beam particle is regarded as a circulating beam particle located outside of the separatrix.

Since the orbits and current values of beam particles that transcend the separatrix are not stable during the formation of the separatrix, that is to say, while the shape of the separatrix is changing, beam particles lost during the formation of the separatrix cannot be used for medical treatment specially in the case of applying a scanning irradiation method.

The beam particles lost during the formation of the separatrix are prevented from reaching a patient with the use of various techniques such as a technique in which the septum magnet is excited after the formation of the separatrix, or a technique in which beam particles extracted during the formation of the separatrix are blocked by installing a magnet for blocking beam particles in the high energy beam transport.

An area that is occupied by circulating beam particles in the horizontal direction phase space, that is to say, the horizontal emittance of the circulating beam is decreased in inversely proportional to the momentum of the circulating beam while the circulating beam is being accelerated.

Therefore, in the case where the energy of a beam extracted from the synchrotron is low (for example, 70 MeV in the case of photon therapy), the attenuation of the horizontal emittance of the beam is not sufficient, with the result that the ratio of beam particles lost during the formation of the separatrix is apt to increase in comparison with in the case where the energy of a beam extracted is high (for example, 220 MeV in the case of photon therapy).

In order to decrease a beam loss during the formation of the separatrix when beams with low energies are extracted from the synchrotron, it is necessary that the area of the separatrix (separatrix size) should be enlarged and the ratio of circulating beam particles located outside of the separatrix at the time when the acceleration is finished should be decreased.

Figure 8:
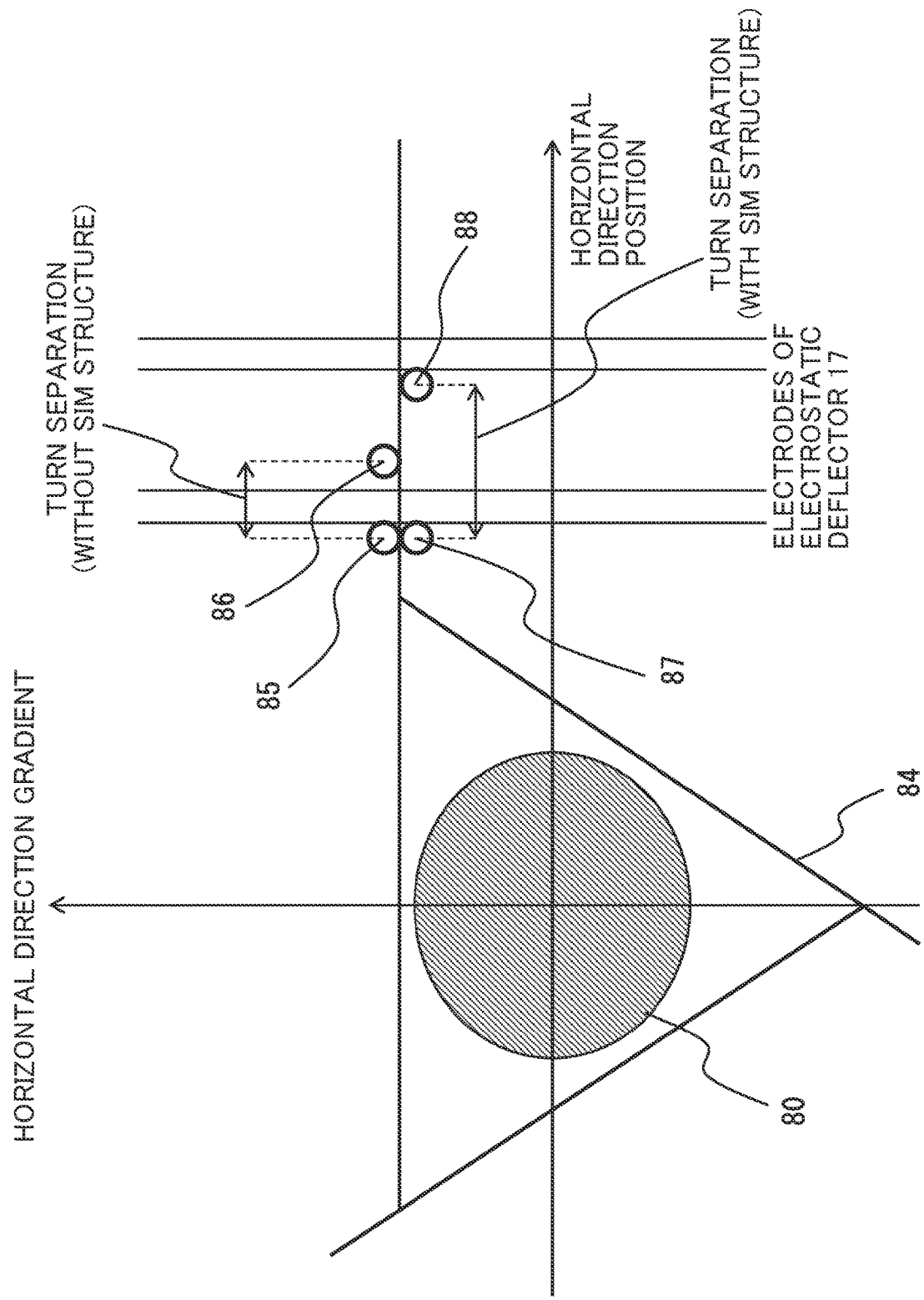
FIG. 8 is a schematic diagram of the horizontal direction phase space distribution of circulating beam particles at the inlet position of the electrostatic deflector of the particle therapy system according to the first embodiment.

The schematic diagram of the horizontal direction phase space distribution of circulating beam particles in the case of the size of the separatrix for extraction being enlarged is shown in FIG. 8. A triangle 84 shows an enlarged separatrix for extraction. White circles 85 and 86 are respectively similar to the white circles 82 and 83 shown in FIG. 7, and the white circles 85 and 86 represent the orbits of an extracted beam particle that is not influenced by the shim structures of the bending magnets, that is to say, the orbits of an extracted beam particle for comparison.

In order to enlarge the size of the separatrix, it is conceivable that the excitation amounts of the sextupole magnets are decreased or the horizontal tunes are held off from the resonant line when a beam is extracted. The enlargement of the separatrix size makes it possible to decrease the ratio of circulating beam particles lost during the formation of the separatrix especially in the low energy region.

On the other hand, in the slow extraction method, there is a negative correlation between the turn separation and the separatrix size. Here, the slow extraction method is a method in which charged particles are extracted bit by bit over a long period of time by setting several hundred milliseconds to several seconds or longer as the pulse widths of extracted beams. As this beam extraction control method, many methods have been examined, and one of the representative methods is a method referred to as a resonant extraction method. This method is a method in which the fact that there is a deep correlation between the cycle of the betatron oscillation of a beam particle that moves with a closed orbit as the center of its movement and the stable circulation of the relevant beam is utilized.

Under the condition that the separatrix size is enlarged, the turn separation of an extracted beam is decreased, and the ratio of beam particles that collide with the electrode inside of the electrostatic deflectors 17 (the electrode nearer to the central orbit) is increased, hence there is a possibility that the efficiency of extracting beams from the synchrotron 10 is decreased.

Here, let the influence that is given to the horizontal direction phase space distribution of circulating beam particles, which are being extracted, by the octupole magnetic field generated by the shim structure of the bending magnet 12 be discussed.

Since, as the amplitude of the horizontal betatron oscillation of a circulating beam particle becomes larger, the horizontal tune of the circulating beam particle more closely approaches the resonant line for extraction by the influence of the octupole magnetic field, the horizontal tunes of beam particles that enter the electrostatic deflector 17 have values closer to the resonant line for extraction than values that the horizontal tunes of circulating beam particles around the periphery of the separatrix have.

Since there is a negative correlation between the distance of the horizontal tune of a circulating beam particle from the resonant line for extraction and the turn separation, a turn separation under the presence of an octupole magnetic field becomes larger than a turn separation in the case of the octupole magnetic field not being taken into consideration, hence a beam loss at the inlet of the electrostatic deflector 17 is decreased.

White circles 87 and 88 represent the orbits of extracted beam particles in the case where an influence exercised on the extracted beam particles by the shim structures of the bending magnets 12 according to this embodiment is taken into consideration.

In this case, since the amplitudes of betatron oscillations around the periphery of the separatrix are smaller than beam particles that enter the electrostatic deflector 17, the horizontal tunes of circulating beam particles are not so much different from those in the case where an octupole magnet field is not taken into consideration.

Therefore, in the presence of an octupole magnetic field due to the shim structures of the bending magnets 12, both beam loss during the formation of the separatrix and beam loss at the inlet of the electrostatic deflector 17 are decreased, hence it becomes possible to improve the efficiency of extracting beams from the synchrotron 10. The improvement of the efficiency of extracting beams from the synchrotron 10 leads to the increase of the amount of current usable for particle therapy, hence it is possible to shorten irradiation time for irradiating a patient 50 with beams and to shorten time required for providing the patient 5 with medical treatment in the particle therapy system 100 according to this embodiment.

In addition, an octupole magnetic field fed to circulating beams is generated by the shim structure of the bending magnet 12 in this embodiment, hence it is not necessary to install an additional magnet for feeding an octupole magnetic field (an octupole magnet) in the synchrotron. Consequently, the straight line part of the synchrotron 10 can be made shorter in this case than in the case where octupole magnets are installed in the straight line part of the synchrotron 10, therefore there is an advantageous effect that the synchrotron 10 can be miniaturized.

Meanwhile, although the above descriptions have been made so far about the case where the shim structure of the bending magnet 12 generates an octupole magnetic field in this embodiment, it is conceivable that a multipole magnet field generated by the bending magnet 12 is a magnetic field other than an octupole magnetic field. If a magnetic field generated by the bending magnet 12 is a multipole magnetic field that makes the horizontal tunes of circulating beam particles having the large amplitudes of horizontal direction betatron oscillations more closely approach the resonant line for extraction, an advantageous effect similar to the advantageous effect that has been described above in this embodiment can be obtained.

Figure 9:
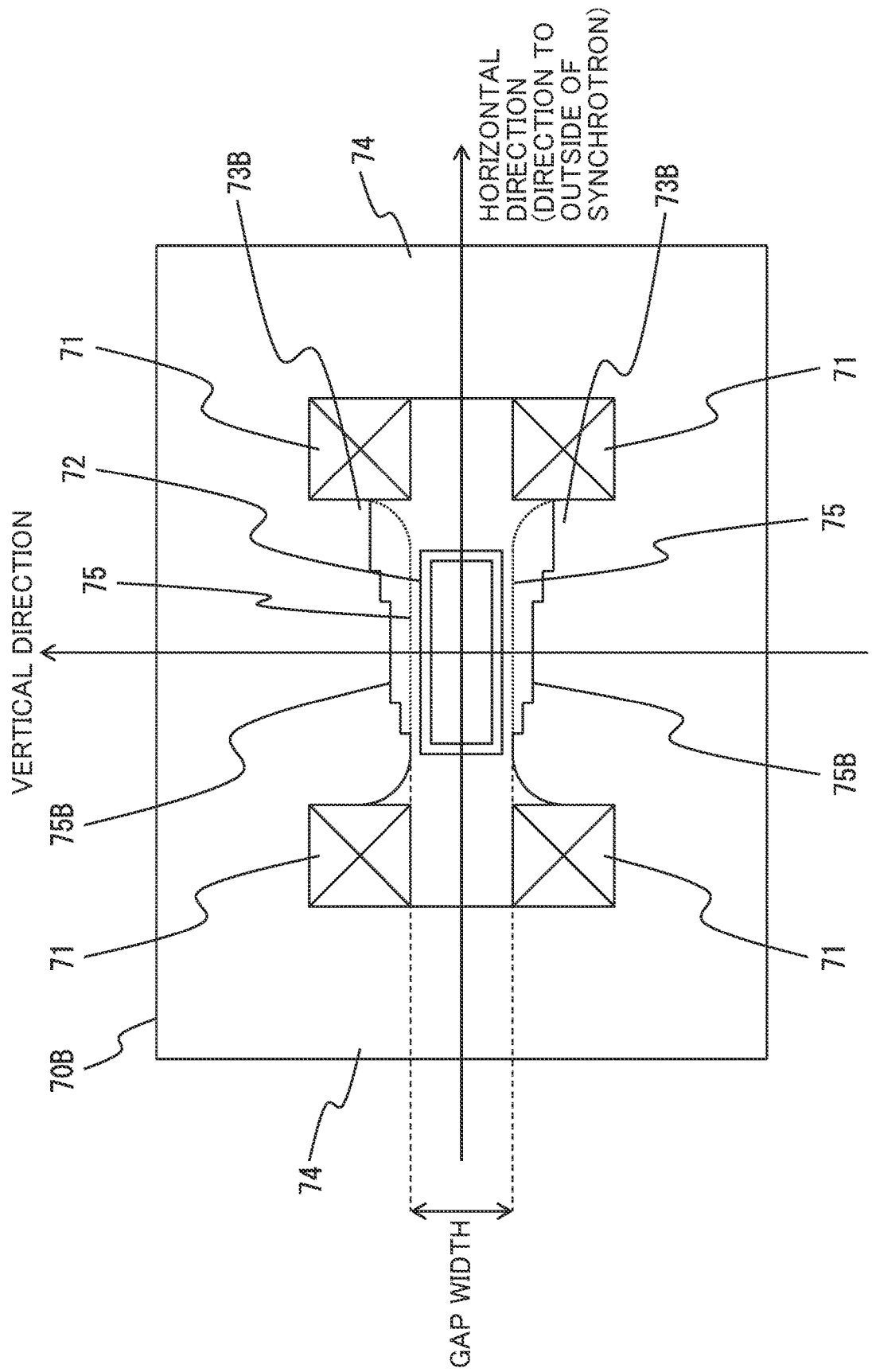
FIG. 9 is a schematic diagram of another example of the shape of the gap width at the traveling direction end of the bending magnet of the particle therapy system according to the first embodiment.

Furthermore, although the case where the gap width of the end of a bending magnet 12 is changed in a cubic function shape in the horizontal direction has been described so far in this embodiment, it is also conceivable that the gap width of the end of the bending magnet 12 is changed in a step-like shape as shown in FIG. 9. Hereinafter, the case where the gap width of the end of the bending magnet 12 is changed in a step-like shape will be explained with reference to FIG. 9. FIG. 9 is a schematic diagram of another example of the shim structure at the traveling direction end of the bending magnet 12.

As shown in FIG. 9, a gap width between the magnetic pole surfaces 75B of magnetic poles 73B in the magnetic body 70B is changed in a step-like shape. In this case, step widths in the vertical direction are set constant, and step widths in the horizontal direction on the central orbit are set wide (for example, about half the width of a horizontal direction range through which a circulating beam passes).

Owing to the magnetic poles 70B, an odd multipole magnetic field can be fed to a circulating beam, hence an advantageous effect similar to the abovementioned advantageous effect obtained in the case where the gap width is changed in a cubic curve shape is obtained.

Second Embodiment

A particle therapy system according to a second embodiment of the present invention will be explained with reference to FIG. 10 to FIG. 12. Components of the second embodiment that are the same as those of the first embodiment will be give the same reference signs and redundant explanations are omitted.

Figure 10:
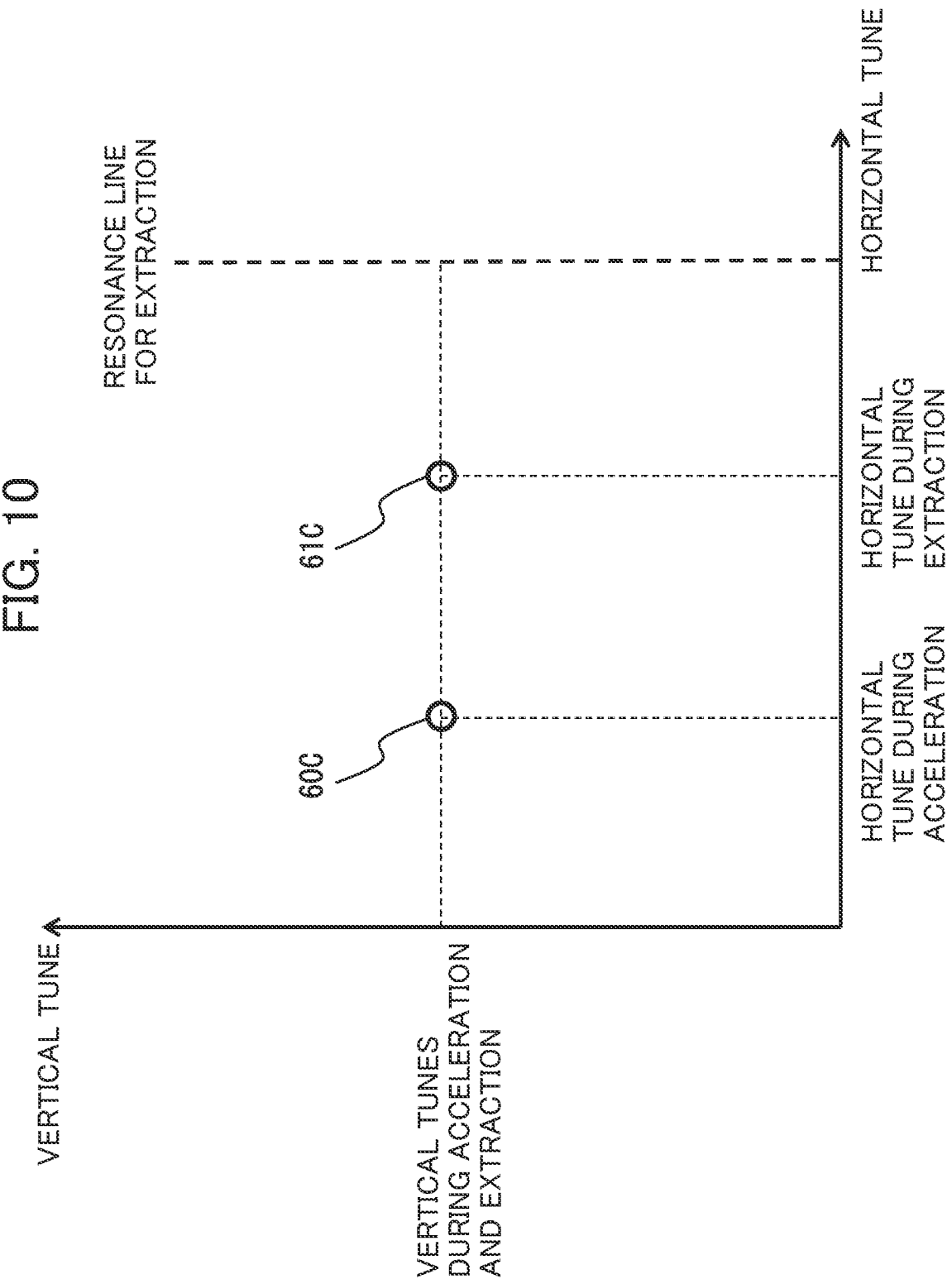
FIG. 10 is a schematic diagram showing the relationship between a resonant line for extraction and the horizontal tune of a synchrotron in a particle therapy system according to a second embodiment of the present invention.

FIG. 10 is a schematic diagram showing the relationship between a resonant line for extraction and the horizontal tune of a synchrotron in the particle therapy system according to this embodiment. FIG. 11 and FIG. 12 are respectively schematic diagrams each of which shows a bending magnet of this embodiment that is viewed from the vertical positive direction.

The relationship between the horizontal tune and vertical tune of the synchrotron of the particle therapy system according to this embodiment is shown in FIG. 10. The horizontal axis in FIG. 10 represents the horizontal tune of the synchrotron, the vertical axis represents the vertical tune of the synchrotron, a white circle 60C represents a combination of the horizontal tune and the vertical tune when a circulating beam is accelerated (an operating point), and a white circle 61C represents a combination of the horizontal tune and the vertical tune when a circulating beam is extracted.

In the synchrotron according to this embodiment, the horizontal tune when a circulating beam is accelerated has a value lower than the resonant line for extraction. In addition, the horizontal tune when a circulating beam is extracted is controlled by quadrupole magnets 13 so that the horizontal tune has a value lower than the resonant line for extraction, and it has a value higher than the horizontal tune when a circulating beam is accelerated (that is to say, it has a value nearer to the resonant line for extraction).

The configuration and control for improving the efficiency of extracting beams from the synchrotron in the particle therapy system 100 according to this embodiment will be explained hereinafter.

As for bending magnets included in the synchrotron according to this embodiment, as is the case with the bending magnets 12 of the first embodiment, shim structures are formed in the regions of the ends of magnetic poles 73B, to which a Rogowski cut is applied, at the inlet side and at the outlet side of each bending magnet 12 of this embodiment for a circulating beam.

As for each shim structure, although the structure of a magnetic body 70C is similar to the traveling direction central part of the magnetic body 70 of the bending magnet 12 according to the first embodiment as shown in FIG. 11, the gap width of a gap varies depending on the horizontal direction position of the gap at each end of the bending magnet according to this embodiment.

To put it concretely, at each end of the bending magnet 12, a gap width that is a distance between the magnetic pole surfaces 75C of magnetic poles 73C in a region at the horizontal direction positive side (outside in the radial direction) is narrower than a gap width on the central orbit, and a gap width in a region at the horizontal direction negative side (inside in the radial direction) is wider than the gap width on the central orbit.

In addition, as shown in FIG. 11, the change amount of the gap width in the range through which the beam passes can be set as a cubic function shape, and a gap width between the magnetic field surfaces 75D of the magnetic poles 73D of a magnetic body 70D can also be made to change in a step-like shape as shown in FIG. 12.

Even in the synchrotron of such an embodiment as this, since the horizontal tune when a beam is extracted has a value lower than the resonant line for extraction, the shim structure of the bending magnet generates a magnetic field distribution that makes the horizontal tune of a circulating beam particle more closely approach the resonant line for extraction as the amplitude of the horizontal betatron oscillation of the circulating beam particle becomes larger.

Since other components and behaviors of the particle therapy system according to this embodiment are almost the same as those of the particle therapy system 100 according to the first embodiment, detailed explanations about them are omitted.

In the particle therapy system according to the second embodiment of the present invention, an advantageous effect that is almost the same as the particle therapy system 100 according to the first embodiment can be obtained.

Others

Furthermore, the present invention is not limited to the above-described embodiments, and various modifications and applications may be made in the present invention. The above embodiments have been described in detail in order to explain the present invention in an easily understood manner, and the present invention is not necessarily limited to particle therapy systems including all the configurations that have been described so far.

List of Reference Signs

10 . . . Synchrotron
12 . . . Bending Magnet
20 . . . High Energy Beam Transport
30 . . . Rotating Gantry
40 . . . Beam Delivery System/Nozzle/Irradiation Nozzle
50 . . . Patient
51 . . . Target Volume (Irradiation Target)
60, 60C . . . Horizontal Tune and Vertical Tune during Acceleration
61, 61C . . . Horizontal Tune and Vertical Tune during Extraction
70, 70B, 70C, 70D . . . Magnetic Body
71 . . . Coil
72 . . . Vacuum Duct
73, 73B, 73C, 73D . . . Magnetic Pole
74 . . . Return Yoke
75, 75A, 75B, 75C, 75D . . . Magnetic Pole Surface 80 . . . Horizontal Direction Phase Space Distribution of Circulating Beam Particles at the Time of Acceleration Being Finished
84 . . . Enlarged Separatrix
87 . . . Position of Beam Particle in Horizontal Direction Phase Space before Running Three Laps of Synchrotron before Entering Electrostatic Deflector
88 . . . Position of Beam Particle Entering Electrostatic Deflector in Horizontal Direction Phase Space
90 . . . Control Apparatus
100 . . . Particle Therapy System

The invention claimed is:

1. A particle therapy system that irradiates an irradiation target with a charged particle beam after the charged particle beam is accelerated by a synchrotron,
wherein the synchrotron has a controller configured to control extracting of the charged particle beam, which circulates in the synchrotron, out of the synchrotron by slow extraction using the resonance of a betatron oscillation,
wherein the synchrotron includes at least one bending magnet that bends the charged particle beam into an arc shape with a radial direction defined by the radius of a circle of which the arc of the arc shape is a part, and the bending magnet further has magnetic poles,
wherein the magnetic poles included in the bending magnet each have a shim structure that generates a magnetic field distribution that makes the horizontal tune of the charged particles more closely approach a resonant line used in the slow extraction, as the amplitude of the horizontal betatron oscillation of a charged particle, included in the charged particle beam, becomes larger, and
wherein the shim structures are formed at the inlet side and the outlet side of the bending magnet,
at the inlet side and the outlet side of the bending magnet, the shim structures are formed such that a distance between magnetic pole surfaces is smaller in a position closer to the center of the circle than a distance between magnetic pole surfaces in a position farther from the center of the circle in a radial direction, and
at a central part of the bending magnet, the central part being disposed between the inlet and the outlet side in a travelling direction, the distances between the magnetic pole surfaces are substantially the same along the radial direction.

2. The particle therapy system according to claim 1,
wherein the value of the horizontal tune of the synchrotron when the beam is extracted from the synchrotron is higher than the value of the horizontal tune of the resonance line, and
the shim structures generate a magnetic field distribution that makes the value of the horizontal tune of the charged particle become lower as the amplitude of the horizontal betatron oscillation of a charged particle included in the charged particle beam becomes larger.

3. The particle therapy system according to claim 1,
wherein the value of the horizontal tune of the synchrotron when a beam is extracted from the synchrotron is lower than the value of the horizontal tune of the resonance line, and
the shim structures generate a magnetic field distribution that makes the value of the horizontal tune of the charged particle becomes higher as the amplitude of the horizontal betatron oscillation of a charged particle included in the charged particle beam becomes larger.

4. The particle therapy system according to claim 1, wherein the shim structures have a step-like shape.

5. The particle therapy system according to claim 1,
wherein all bending magnets installed in the synchrotron have shim structures of the same shapes.

6. The particle therapy system according to claim 1,
wherein the bending magnet has a gap between the magnetic poles through which a vacuum duct passes, and
wherein the shim structures are formed on facing surfaces of the magnetic poles in such a manner that a size of a vacuum duct in the direction between the magnetic poles in the synchrotron is constant.

\* \* \* \* \*